United States Patent
Daskalon et al.

(10) Patent No.: US 6,413,660 B1
(45) Date of Patent: Jul. 2, 2002

(54) HIGH-STRENGTH DENTAL RESTORATIONS

(75) Inventors: Gregg Daskalon, Orange; Ajit Karmaker, Wallingford; Elie Zammarieh, Milford; Martin L. Schulman, Orange; Arun Prasad, Cheshire, all of CT (US); Carlino Panzera, Bellemead, NJ (US); Dmitri Brodkin, West Orange, NJ (US); Paul Panzera, Mt. Holly, NJ (US)

(73) Assignee: Jeneric/Pentron, Inc., Wallingford, CT (US)

( * ) Notice: Subject to any disclaimer, the term of this patent is extended or adjusted under 35 U.S.C. 154(b) by 0 days.

(21) Appl. No.: 09/330,665

(22) Filed: Jun. 11, 1999

Related U.S. Application Data

(60) Provisional application No. 60/089,150, filed on Jun. 12, 1998, and provisional application No. 60/094,612, filed on Jul. 3, 1998.

(51) Int. Cl.[7] .................................................. B32B 9/00
(52) U.S. Cl. ........................... 428/699; 428/70; 428/76; 428/697; 428/702; 433/218; 433/212.1; 433/222.1
(58) Field of Search ............................ 428/70, 76, 404, 428/697, 699, 701, 702, 448; 433/218, 223, 212.1, 222.1

(56) References Cited

U.S. PATENT DOCUMENTS

| | | |
|---|---|---|
| 3,066,112 A | 11/1962 | Bowen |
| 3,179,623 A | 4/1965 | Bowen |
| 3,194,784 A | 7/1965 | Bowen |
| 3,423,829 A | 1/1969 | Halpern |
| 3,488,847 A | 1/1970 | Pettrow |
| 3,751,399 A | 8/1973 | Lee |
| 3,926,906 A | 12/1975 | Lee |
| 4,028,325 A | 6/1977 | King |
| 4,364,731 A | 12/1982 | Norling |
| 4,475,892 A | 10/1984 | Faunce |
| 4,544,359 A | 10/1985 | Waknine |
| 4,547,531 A | 10/1985 | Waknine |
| 4,595,598 A | 6/1986 | De Luca |
| 4,652,459 A | 3/1987 | Engelhardt |
| 4,681,538 A | 7/1987 | Deluca |
| 4,684,555 A | 8/1987 | Neumeyer |
| 4,717,341 A | 1/1988 | Goldberg |
| 4,737,411 A | 4/1988 | Graves |
| 4,741,699 A * | 5/1988 | Kosmos |

(List continued on next page.)

OTHER PUBLICATIONS

Kappert, H.F., Knode, H., In–Ceram: Testing a new ceramic material, Quintessence Dental Technology, vol. 16, 87–97, 1993.

Webster's II New College Dictionary, p. 366–367, (Boston, New York 1995) no month.

* cited by examiner

*Primary Examiner*—Deborah Jones
*Assistant Examiner*—Jennifer McNeil
(74) *Attorney, Agent, or Firm*—Ann M. Knab, Esq.

(57) ABSTRACT

High strength ceramic components for use in dental applications are provided with a bonding layer disposed thereon to increase the bonding properties of the ceramic component in order that the ceramic component may better bond to a resin material, ceramic material or composite material. Moreover, the bonding layer provides strength to the ceramic component by forming a compressive layer thereon.

The ceramic component may be partially or fully embedded in composite material. The ceramic component is bonded to the composite material either by mechanical means, chemical means or both. The material may be placed directly on the ceramic component. Alternatively, the structural component is coated with a bonding layer to provide adhesion between the composite or like material and the structural component.

17 Claims, 2 Drawing Sheets

U.S. PATENT DOCUMENTS

| | | |
|---|---|---|
| 4,798,536 A | 1/1989 | Katz |
| 4,820,545 A | 4/1989 | Negrych |
| 4,826,430 A | 5/1989 | Chen |
| 4,894,012 A | 1/1990 | Goldberg |
| 4,895,516 A | 1/1990 | Hulten |
| 4,948,366 A | 8/1990 | Horn |
| 4,983,182 A | 1/1991 | Kijima |
| 4,988,362 A | 1/1991 | Toriyama |
| 5,024,711 A | 6/1991 | Gasser |
| 5,077,079 A | 12/1991 | Kawamura |
| 5,118,296 A * | 6/1992 | Eldred |
| 5,217,375 A * | 6/1993 | Oden et al. |
| 5,276,068 A | 1/1994 | Waknine |
| 5,342,201 A * | 8/1994 | Oden |
| 5,346,717 A | 9/1994 | McCrory |
| 5,444,104 A | 8/1995 | Waknine |
| 5,525,385 A | 6/1996 | Weinstein |
| 5,591,030 A * | 1/1997 | Thiel et al. |
| 5,614,330 A | 3/1997 | Panzera |
| 5,676,997 A | 10/1997 | Okuyama |
| 5,707,231 A | 1/1998 | Watt |
| 5,711,492 A | 1/1998 | Cheladze |
| 5,788,498 A | 8/1998 | Wohlwend |
| 5,849,068 A * | 12/1998 | Hofmann et al. |
| 6,001,896 A | 12/1999 | Ueno |
| 6,001,897 A | 12/1999 | Dickens |
| 6,013,694 A | 1/2000 | Jia |
| 6,120,591 A | 9/2000 | Brodkin |

\* cited by examiner

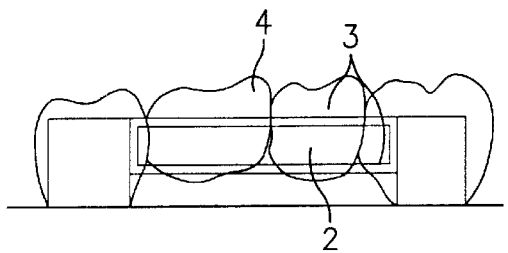
FIG. 1
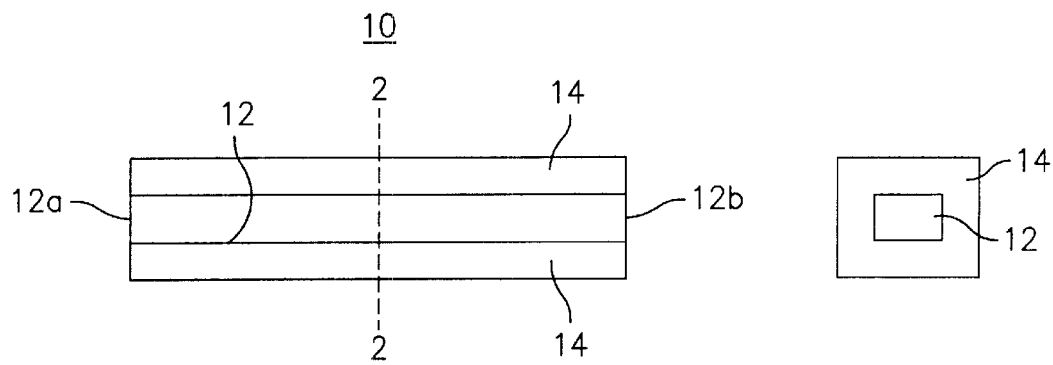
FIG. 2
FIG. 3
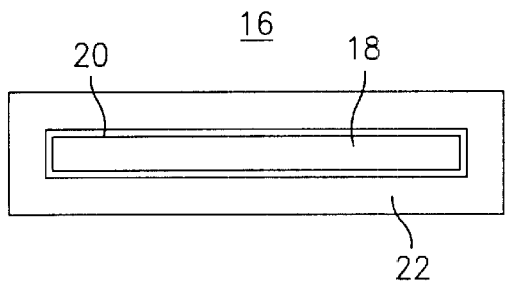
FIG. 4
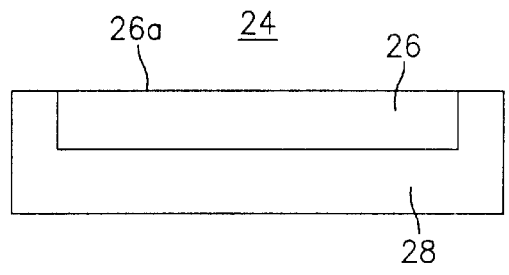
FIG. 5
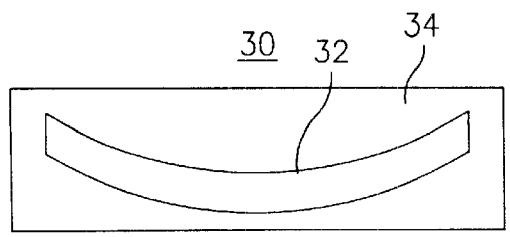
FIG. 6
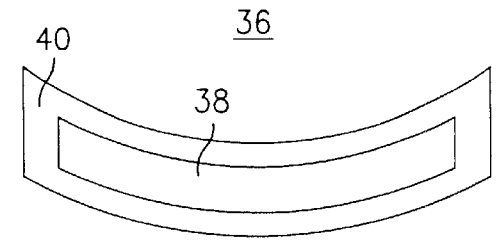
FIG. 7

HIGH-STRENGTH DENTAL RESTORATIONS

This application claims priority to Provisional Application Serial No. 60/089,150 filed on Jun. 12, 1998 and Provisional Application Serial No. 60/094,612 filed on Jul. 3, 1998 both which are hereby incorporated by reference.

TECHNICAL FIELD

The present invention relates generally to dental restorations and more specifically to bonding layers for ceramic components used in dental restorations and methods of making thereof. The invention is also directed to high strength ceramic components embedded in composite materials for use as dental materials.

BACKGROUND OF THE INVENTION

Strength and reliability are important factors to consider when manufacturing dental restorations. Dental restorations must be able to withstand the normal mastication forces and stresses that exist within an oral environment. Different stresses are observed during mastication of different types of food, which can be experimentally measured by placing, for example, a strain gauge in inlays on the tooth. Stresses differ depending not only on the type of food, but also on the individual. For example, stress values may range from 570 to 2300 lb/inch$^2$ for a single chewing thrust on a piece of meat and from 950 to 2400 lb/inch$^2$ for a single thrust on a biscuit. The physical properties of dental restorations must be adequate to withstand the stresses applied by the repetitive forces of mastication.

Ceramic materials have proven to be reliable in the fabrication of single unit dental restorations. U.S. Pat. No. 4,798,536 to Katz and an article by Kabbert and Knode entitled "Inceram: Testing a New Ceramic Material", Vol.4, pp 87–97(1993) each disclose ceramic compositions having leucite therein to provide strength and reliability to dental restorations. The strength of the materials is in the area of 170 MPa which is much higher than that of conventional porcelain which exhibits strengths of about 70 MPa. Nevertheless, the strength a nd/or toughness values of the aforementioned ceramic materials may not be adequate for the fabrication of multiple unit restorations.

There is a need to provide high strength, ceramic restorations having structural integrity and reliability and optimum bonding properties. It is desirable to produce high strength ceramic restorations which are compatible with a wide range of cost-effective polymeric based dental materials.

SUMMARY OF THE INVENTION

These and other objects and advantages are accomplished by the composition and method of manufacture of the present invention directed to high strength ceramic components for use in dental applications. In accordance with one embodiment herein, a bonding layer is disposed on a ceramic component to increase the bonding properties of the ceramic component in order that the ceramic component may better bond to a resin material, ceramic material or composite material. Moreover, the bonding layer provides strength to the ceramic component by forming a compressive layer thereon.

In accordance with another embodiment herein, a ceramic component is partially or fully embedded or encapsulated in composite material. The ceramic component is bonded to the composite material either by mechanical means, chemical means or both. The composite material may be placed directly on the ceramic component. Alternatively, the structural component is coated with a bonding layer to provide adhesion between the composite or like material and the structural component.

In accordance with yet another embodiment herein, silicon dioxide is deposited on the surface of the structural component in the form of colloidal silica, silane, tetra ethyl orthosilicate, or a similar silica precursor and heat treated to form a bonding layer which bonds the structural component to a resin, ceramic or composite material.

The resultant structural component is useful in the fabrication of dental appliances and restorations such as orthodontic retainers, bridges, space maintainers, tooth replacement appliances and splints.

BRIEF DESCRIPTION OF THE DRAWINGS

Features of the present invention are disclosed in the accompanying drawings, wherein similar reference characters denote similar elements throughout the several views, and wherein:

FIG. 1 shows a ceramic bar and bonding layer in accordance with the present invention, FIG. 2 shows a ceramic bar embedded in composite material in accordance with the present invention;

FIG. 3 shown a cross-sectional view at line 2—2 of the component in FIG. 2;

FIG. 4 shows a ceramic bar with a bonding layer deposited thereon and embedded in composite material in accordance with the present invention;

FIG. 5 shows a ceramic bar partially embedded in composite material in accordance with the present invention;

FIG. 6 shows a curved ceramic bar embedded in composite material in accordance with the present invention;

FIG. 7 shows a curved ceramic bar embedded in composite material that follows the contour of the ceramic bar in accordance with the present invention;

DETAILED DESCRIPTION OF THE INVENTION

Figure 8:
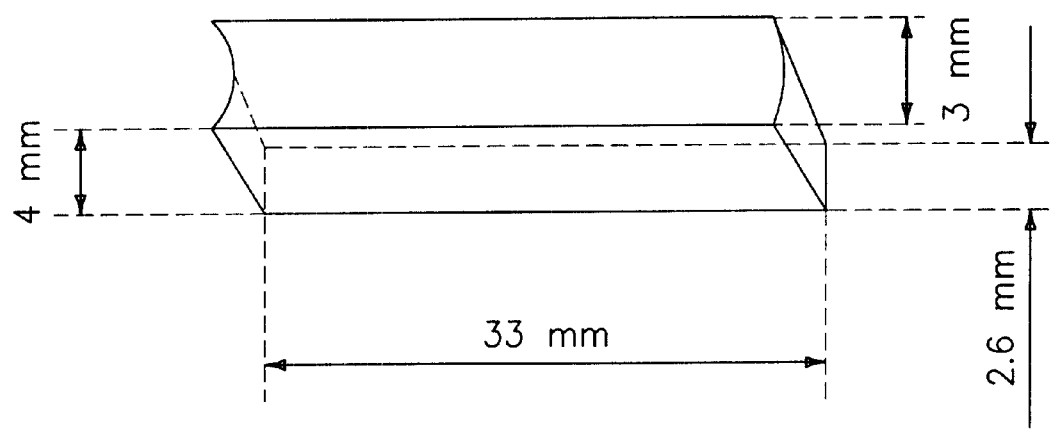
FIG. 8 shows the size and shape of a bar which was used in the examples herein.

The present invention is directed to high-strength structural ceramic components for use in dental applications. In one embodiment herein, a high-strength structural component is provided having a bonding layer disposed thereon. The bonding layer is deposited on the ceramic component to increase the bonding properties of the ceramic component in order that the ceramic component may better bond to a resin material, ceramic material or composite material such as commercially available Sculpture® composite from Jeneric/Pentron, Inc., Wallingford, Conn. or commercially available OPC® porcelain from Jeneric/Pentron, Inc., Wallingford, Conn. Moreover, the bonding layer provides strength to the ceramic component by forming a compressive layer thereon. The resultant structural component is useful in the fabrication of dental appliances and restorations such as orthodontic retainers, bridges, space maintainers, tooth replacement appliances and splints and further as restorations as set forth in U.S. Pat. No. 5,614,330 to Panzera et al., U.S. Pat. Nos. 4,717,341 and 4,894,012 to Goldberg, and copending commonly assigned U.S. Ser. No. 09/133,582 all of which are incorporated by reference herein.

The structural components may be fabricated of a high strength ceramic material such as alumina, zirconia, SIALON, mullite, titanium oxide, magnesium oxide and composites or mixtures thereof. The flexural strength of the ceramic components is typically greater than about 400 MPa and preferably in the range of about 500 MPa to about 1200 MPa. The structural components are preferably in the form of bars or pontics. The bars may be of any cross-sectional configuration effective to provide strength and stiffness to the finished dental appliance. Examples of cross-sectional configurations of the bars include square, rectangular, triangular, rhomboidal, ovoidal, and cylindrical shapes. The bars may be straight or curved depending upon the placement or use thereof In accordance with one embodiment of the method of the invention, the structural components are coated with a bonding layer to provide adhesion between a resin or like material and the structural component. It is preferable that the bonding layer be able to easily bond to a coupling agent such as a silane compound. Suitable bonding layers include but are not limited to silica, silicates, aluminates, phosphates, fluorates, aluminosilicates, silica-rich glasses, zirconates and titanates. Preferably, silica containing materials such as porcelain materials such as commercially available ColorMatch™ porcelain from Jeneric/Pentron Inc., Wallingford, Conn. and Vitadurn™ porcelain from Vita Zahnfabrik, Bad Sackingen, Germany or silica are used as the bonding layer. The layer may be applied in any known manner including, but not being limited to, a sol/gel deposition followed by pyrolysis, fusing, sputtering, chemical vapor deposition, ion bombardment, and vacuum deposition. If the bonding layer is fused to the structural component, the fusion temperature should be lower than that of the structural component. The fusion temperature of the bonding material is typically in the range of about 400° C. to about 1500° C. Moreover, it is preferable that the bonding layer has a coefficient of thermal expansion slightly lower than that of the structural component. Furthermore, it is desirable that the bonding layer exhibits good wetting properties.

In accordance with a second embodiment of the method of the invention, silicon dioxide is deposited on the surface of the structural component in the form of colloidal silica, silane, tetra ethyl orthosilicate, or a similar silica precursor. The silicon dioxide may be pure silicon dioxide. The component with the layer thereon is heated to a sufficiently high temperature in the range of about 400° C. to about 1400° C., preferably about 600° C. to about 1300° C. to allow the silica to react with the structural component to form a bond. For example, if the structural component comprises alumina, the silica reacts therewith to form a thin layer of mullite. If the structural component comprises zirconia, the silica reacts therewith to form zircon. The mullite and zircon each possess a lower thermal expansion than the alumina and zirconia, respectively, thereby forming a compressive layer on the structural components further increasing the strength.

In accordance with the method of the invention, the bonding layer can be abraded or etched by methods known in the art such as sand blasting or acid etching. The layer may then be primed with a coupling agent. U.S. Pat. Nos. 5,444,104, 4,547,531 and 4,544,359 all to Waknine, which are incorporated by reference herein, discuss suitable etching and priming procedures. Suitable coupling agents include silane compounds such as organo-silane agents. Exemplary silane agents include gamma-methacryloxy propyltrimethoxysilane which is available from OSi Specialties, Inc., Friendly, W.Va. under the name Silquest A-174, gamma-aminopropyl triethoxysilane, vinyl trichlorosilane and styrylamine functional silane.

In accordance with another embodiment herein, the present invention is directed to a high-strength structural ceramic component partially or fully embedded or encapsulated in composite material. The composite material may be any known composite material such as a resin or polymeric material combined with particulate and/or fiber material. Preferably, the composite is a polymeric material having particulate therein such as commercially available Sculptures ® composite available from Jeneric/Pentron Inc., Wallingford, Conn., or polymeric material reinforced with fiber and/or particulate such as commercially available FibreKor® composite from Jeneric/Pentron, Inc., Wallingford, Conn. The ceramic component is bonded to the composite material either by mechanical means, chemical means or both. Mechanical bonding occurs after the ceramic component is embedded in the composite material and the composite material is cured. To aid in the mechanical bonding of the composite material to the ceramic component, the ceramic component may be treated prior to covering with composite material. Treatment may include etching, abrading and the like. Chemical bonding of the ceramic to composite material may involve organically modifying the surface of the ceramic such as through application of a silane or other coupling agent to the surface of the ceramic. Preferably, the composite material completely encapsulates the ceramic component. This then allows for easier carving or grinding or other similar modification to the component to form the shape desired since bridges, space maintainers, tooth replacement appliances and splints each require some customization to adequately fit within the patient's mouth. The ceramic component may be difficult to carve into complicated or difficult shapes. The composite material thereon allows for such modification. The resultant structural component is useful in the fabrication of dental appliances and restorations such as orthodontic retainers, bridges, space maintainers, tooth replacement appliances and splints and further as restorations set forth in U.S. Pat. No. 5,614,330 to Panzera et al., U.S. Pat. Nos. 4,717,341 and 4,894,012 to Goldberg, and copending commonly assigned U.S. Ser. No. 09/133,582, all of which are incorporated by reference herein.

In accordance with an embodiment of the method of the invention, the composite material is placed directly on the ceramic component. The composite material may be wound around the ceramic component or molded, pressed or deposited in any known fashion or method. The composite material may be oriented in one or more directions. For example, if fiber reinforced composite material is used, it may be wound around the ceramic component. One layer may be oriented perpendicular to the length of the ceramic component and the next layer may be oriented parallel to the length of the ceramic component, alternating the direction as layers are applied thereto. Commercially available Fibrekor® fiber reinforced composite from Jeneric/Pentron Inc., Wallingford, Conn. may be used to build the fiber reinforced composite around the ceramic component.

In accordance with an alternative embodiment of the method of the invention, prior to partially or fully encapsulating or embedding the structural component in composite material, the structural component is coated with a bonding layer as set forth above to provide adhesion between the composite material and the structural component.

Additionally, the bonding layer provides strength to the ceramic component by forming a compressive layer thereon. A coupling agent may be applied to the structural component prior to application of the bonding layer. It is preferable that the bonding layer be able to easily bond to a coupling agent such as a silane compound. Suitable bonding layers include but are not limited to silica, silicates, aluminates, phosphates, fluorates, aluminosilicates, silica-rich glasses, zirconates and titanates. The layer may be applied in any known manner including, but not being limited to, fusing, sputtering, chemical vapor deposition, ion bombardment, and vacuum deposition. If the bonding layer is fused to the structural component, the fusion temperature should be lower than that of the structural component. Moreover, it is preferable that the bonding layer has a coefficient of thermal expansion slightly lower than that of the structural component. Furthermore, it is desirable that the bonding layer exhibits good wetting properties.

In accordance with yet another embodiment of the method of the invention, prior to partially or fully encapsulating or embedding the structural component in composite material, silicon dioxide is deposited on the surface of the structural component in the form of colloidal silica, silane, tetra ethyl orthosilicate, or a similar silica precursor. The silicon dioxide may be pure silicon dioxide. The component with the layer thereon is heated to a sufficiently high temperature to allow the silica to react with the structural component to form a bond. For example, if the structural component comprises alumina, the silica reacts therewith to form a thin layer of mullite. If the structural component comprises zirconia, the silica reacts therewith to form zircon. The mullite and zircon each possess a lower thermal expansion than the alumina and zirconia, respectively, thereby forming a compressive layer on the structural components further increasing the strength.

The composite material used above may be fully or partially polymerized using photo, chemical or thermal means under controlled pressure or atmospheric presssure. The resin or polymeric component can be selected from those known in the art of dental materials, including those listed in commonly assigned U.S. patent application Ser. No. 08/951,414, filed Oct. 16, 1997, which is incorporated by reference herein. The polymeric matrix materials include but are not limited to expandable monomers, liquid crystal monomers, ring-opening monomers, polyamides, acrylates, polyesters, polyolefins, polymides, polyarylates, polyurethanes, vinyl esters or epoxy-based materials. Other polymeric matrices include styrenes, styrene acrylonitriles, ABS polymers, polysulfones, polyacetals, polycarbonates, polyphenylene sulfides, and the like. These polymeric matrices are derived from curing polymeric matrix precursor compositions. Such precursor compositions are well-known in the art, and may be formulated as one-part, two-part, or other compositions, depending on the components.

Preferred materials include those based on acrylic and methacrylic monomers, for example those disclosed in U.S. Pat. Nos. 3,066,112, 3,179,623, and 3,194,784 to Bowen; U.S. Pat. Nos. 3,751,399 and 3,926,906 to Lee et al.; and commonly assigned U.S. Pat. No. 5,276,068 to Waknine and application Ser. No. 08/998,849 filed on Dec. 29, 1997, all of which are herein incorporated by reference in their entirety. Especially preferred methacrylate monomers include the condensation product of bisphenol A and glycidyl methacrylate, 2,2'-bis[4-(3-methacryloxy-2-hydroxy propoxy)-phenyl]propane (hereinafter abbreviated BIS-GMA), the condensation product of ethoxylated bisphenol A and glycidyl methacrylate, (hereinafter EBPA-DMA), and the condensation product of 2 parts hydroxymethyl-methacrylate and 1 part triethylene glycol bis (chloroformate) (hereinafter PCDMA). Polyurethane dimethacrylates (hereinafter abbreviated to PUDMA) are also commonly-used principal polymers suitable for use in the present invention.

The polymeric matrix precursor composition may further comprise a co-polymerizable diluent monomer. Such monomers are generally used to adjust the viscosity of the polymerizable composition, which affects wettability of the composition. Suitable diluent monomers include, without limitation, hydroxyalkyl methacrylates, such as 2-hydroxyethyl methacrylate, 1,6-hexanediol dimethacrylate, and 2-hydroxypropyl methacrylate; glyceryl dimethacrylate; ethyleneglycol methacrylates, including ethyleneglycol methacrylate, diethyleneglycol dimethacrylate, triethyleneglycol dimethacrylate and tetra-ethyleneglycol dimethacrylate; or diisocyanates, such as 1,6-hexamethylene diisocyanate. Triethyleneglycol dimethacrylate (TEGDMA) is particularly preferred for use in the present invention.

The polymeric matrix precursor composition typically includes polymerization initiators, polymerization accelerators, ultra-violet light absorbers, anti-oxidants, fluorescent whitening agents, and other additives well known in the art. The polymer matrices may be visible light curing, self-curing, dual curing, and vacuum-, heat-, and pressure-curable compositions as well as any combination thereof. Visible light curable compositions employ light-sensitive compounds such as benzil diketones, and in particular, dl-camphorquinone in amounts ranging from about 0.05 to 0.5 weight percent. UV absorbers are particularly desirable in the visible light curable compositions in order to avoid discoloration of the resin form any incident ultraviolet light. Suitable UV absorbers are the various benzophenones, particularly UV-9 and UV-5411 available from American Cyanamid Company, and benzotriazoles known in the art, particularly 2-(2'-hydroxy-5'-methylphenyl)-benzotriazole, sold under the trademark TINUVIN P by Ciba-Geigy Corporation, Ardsley, N.Y. in amounts ranging from about 0.05 to about 5.0 weight percent.

In the self curing compositions, a polymerization accelerator may be included in the polymerizable monomer composition. The polymerization accelerators suitable for use include the various organic tertiary amines well known in the art, generally aromatic tertiary amines, such as dimethyl-p-toluidine, dihydroxyethyl-p-toluidine and the like, in amounts ranging from about 0.05 to about 4.0 weight percent, and generally acrylate derivatives such as dimethylaminoethyl methacrylate and particularly, diethylaminoethyl methacrylate in amounts ranging from about 0.05 to 0.5 weight percent.

The heat and pressure curable compositions include, in addition to the monomeric components, a heat cure initiator such as benzoyl peroxide, 1,1'-azobis (cyclohexanecarbonitrile), or other suitable free radical initiators. Particularly suitable free radical initiators are lauroyl peroxide, tributyl hydroperoxide, AIBN and, more particularly benzoyl peroxide or 1,1'-azobis (cyclohexanecarbonitrile).

The polymeric matrix may further comprise at least one filler known in the art and used in dental restorative materials, including reinforcing fibers as set forth in U.S. Pat. Nos. 4,717,341 and 4,894,012 to Goldberg et al, and copending commonly assigned U.S. application No. 60/078, 347 filed on Mar. 17, 1998, all of which are incorporated by reference herein in their entirety. Suitable fillers are those capable of being covalently bonded to the polymeric matrix itself or to a coupling agent that is covalently bonded to both. Examples of suitable filling materials include but are not limited to those known in the art such as silica, silicate glass, quartz, barium silicate, strontium silicate, barium borosilicate, strontium borosilicate, borosilicate, lithium silicate, amorphous silica, ammoniated or deammoniated calcium phosphate and alumina, zirconia, tin oxide, and titania. Particularly suitable fillers for dental filling-type materials prepared in accordance with this invention are those having a particle size ranging from about 0.1–5.0 microns with a silicate colloid of 0.001 to about 0.07 microns and prepared by a series of milling steps comprising wet milling in an aqueous medium, surface etch milling and silanizing milling in a silane solution. Some of the aforementioned inorganic filling materials are disclosed in commonly-assigned U.S. Pat. Nos. 4,544,359 and No. 4,547,531 to Waknine, the pertinent portions of which are incorporated herein by reference.

The reinforcing fiber element of the polymeric composite preferably comprises glass, carbon, graphite, polyaramid, or other fibers known in the art, such as polyesters, polyamides, and other natural and synthetic materials compatible with the polymeric matrix. Some of the aforementioned fibrous materials are disclosed in commonly assigned copending U.S. patent application Ser. No. 08/907,177, which is incorporated herein by reference. The fibers may further be treated, for example silanized, to enhance the bond between the fibers and the polymeric matrix. The fibers preferably take the form of long, continuous filaments, although the filaments may be as short as 3 to 4millimeters. Shorter fibers of uniform or random length might also be employed. Preferably, the fibers are at least partially aligned and oriented along the longitudinal dimensions of the wire. However, depending on the end use of the composite material, the fibers may also be otherwise oriented, including being normal or perpendicular to that dimension.

In all embodiments set forth above, the bonding layer may be applied in any thickness sufficient to create a bond between the structural component and the outer resin, ceramic or composite layer. Preferably, the thickness of the bonding layer is about 5 microns to about 100 microns. The layer may be applied to all sides of the structural component or only those sides which will require an outer surface layer thereon to form the dental restoration. Preferably, all sides of the structural component are coated. After the bonding layer has cured, it can be abraded or etched by methods known in the art such as sand blasting or acid etching. The layer may then be primed with a coupling agent. U.S. Pat. Nos. 5,444,104, 4,547,531 and 4,544,359 all to Waknine, which are incorporated by reference herein, discuss suitable etching and priming procedures. Suitable coupling agents include silane compounds such as organo-silane agents. Exemplary silane agents include gamma-methacryloxy propyltrimethoxysilane which is available from OSi Specialties, Inc., Friendly, W.Va. under the name Silquest A-174, gamma-aminopropyl triethoxysilane, vinyl trichlorosilane and styrylamine functional silane.

After application of the coupling agent, the structure may be readily bonded to resin, ceramic or composite material in order to manufacture a dental restoration or appliance.

FIGS. 1 through 7 show examples of dental materials manufactured in accordance with the present invention. FIG. 1 shows a cross-sectional view of a ceramic component 2 with a bonding layer 3 thereon and resin material 4 formed on bonding layer 3. FIG. 2 shows a cross-sectional view of a dental material 10 comprising a ceramic component 12 partially embedded in particulate filled composite material 14. All sides of component 12 are embedded except for ends 12a and 12b which are exposed and not covered by composite material 14. FIG. 3 is a cross-sectional view of FIG. 2 at line 2—2. FIG. 4 shows a cross-sectional view of a dental material 16 having a ceramic component 18 covered with a bonding layer 20 and fully embedded on all sides in a fiber reinforced composite material 22. FIG. 5 shows a cross-sectional view of a dental material 24 with a ceramic component 26 partially embedded in composite material 28. The upper side 26a of ceramic component 26 is exposed. FIG. 6 shows a cross-sectional view of a dental material 30 comprising a ceramic component 32 fully embedded in fiber reinforced composite material 34. FIG. 7 shows a cross-sectional view of a dental material 36 having a ceramic component 38 fully embedded in fiber reinforced composite material 40 which follows the contour of the ceramic material 38. In each of the FIGURES, the coated structural materials shown may be further modified by grinding, cutting, sawing, machining or likewise modifying to any shape desired to fabricate a dental appliance or restoration. The outer composite material is easy to work with in comparison to the ceramic component which may be difficult to cut or grind. The outer material may be easily cut to any desired shape or size.

EXAMPLES

Figure 9:
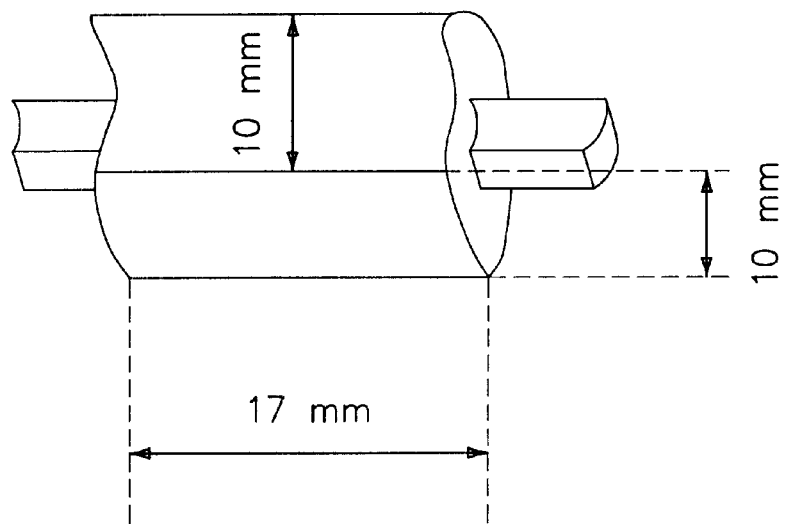
FIG. 9 shows a veneering material on the bar of FIG. 8 which was used in the examples for testing bond strength.

Three-point flexural tests were conducted on zirconia bars having dimensions of 33 mm×4 mm×3 mm whereby the 3 mm side tapers to 2.6 mm and the top of the bar is slightly concave as shown in FIG. 8. The bars were treated as set forth in the Table 1 below to determine the bonding strength between the bars and the veneering layer. The veneering layer was applied along the length of the bar at a span of about 17 mm×10 mm×10 mm as shown in FIG. 9. In example 1, zirconia bars without prior treatment and without a bonding material were tested for strength. In example 2, zirconia bars were heated and a veneering layer was applied without an intermediate bonding layer. In example 3, zirconia bars were heat treated and therafter coated with a layer of silane. A veneering layer was thereafter applied. In examples 4 through 6, zirconia bars were coated with a bonding layer and heat treated thereafter to fuse the layer thereto. Veneering layers were then applied to the bonding layer with or without surface treatment or a coupling agent as set forth in Table 1. Table 1 provides the three-point flexural test results for the various examples.

TABLE 1

| Material | Bonding Material | Heat Treatment | Surface Treatment | Veneering Layer | Bending Load (lbs) |
|---|---|---|---|---|---|
| 1. Zirconia Bars (as received) | none | none | none | none | 227 |
| 2. Zirconia Bars | none | 960° C. | none | Sculpture ® Resin | 198 |
| 3. Zirconia Bars | none | 960° C. | silane | Sculpture ® Resin | 189 |
| 4. Zirconia Bars | Tyspar ® porcelain** | 857° C. | silane & thinning liquid | Sculpture ® Resin | 226 |
| 5. Zirconia Bars | Vitadurn ™ porcelain*** | 960° C. | none | Sculpture ® Resin | 210 |
| 6. Zirconia Bars | Color-Match ™ porcelain* | 938° C. | silane & thinning liquid | Sculpture ® Resin | 215 |

*ColorMatch is a trademark of Jeneric/Pentron Inc., Wallingford, CT.
**Tyspar is a registered trademark of American Thermocraft Corporation, Somerset, NJ.
***Vitadurn is a trademark of Vita Zahnfabrik, Bad Sackingen, Germany.

The results in Table 1 show the bond strength obtained between the zirconia bars and the resin materials when an intermediate bonding layer is used. Example 1 exhibits the strength of the zirconia. The bars which were coated with a bonding material (Examples 4–6) show strengths similar to strengths of the as received bars of Example 1 which had no prior treatment. When no bonding layer was used, the bonding strength decreased. Dental materials and restorations having high strength structural components are appreciated by the invention wherein a bonding layer is applied to the ceramic component by fusion, sputtering, chemical vapor deposition, ion bombardment, vacuum deposition and the like to achieve a layer to which a resin, composite, ceramic, or like material will easily bond to.

While various descriptions of the present invention are described above, it should be understood that the various features can be used singly or in any combination thereof. Therefore, this invention is not to be limited to only the specifically preferred embodiments depicted herein.

Further, it should be understood that variations and modifications within the spirit and scope of the invention may occur to those skilled in the art to which the invention pertains. Accordingly, all expedient modifications readily attainable by one versed in the art from the disclosure set forth herein that are within the scope and spirit of the present invention are to be included as further embodiments of the present invention. The scope of the present invention is accordingly defined as set forth in the appended claims.

What is claimed is:

1. A dental material comprising:
   a bar or pontic fabricated of a high strength ceramic material and wherein the bar or pontic is completely encapsulated in a composite material.

2. The dental material of claim 1 wherein the ceramic is comprised of at least one of alumina, zirconia, SIALON, mullite, titanium oxide, magnesium oxide, and mixtures thereof.

3. The dental material of claim 1 further comprising one or more ceramic bonding layers located between the high strength ceramic material and the composite material.

4. The dental material of claim 3 wherein the bonding layer has a thermal expansion that is slightly lower than a thermal expansion of the high strength ceramic material.

5. The dental material of claim 3 wherein the bonding layer is selected from silica, silicates, aluminates, phosphates, fluorates, aluminosilicates, silica-rich glasses, zirconates and titanates.

6. The dental material of claim 1 wherein the composite material is fiber-reinforced composite material.

7. The dental material of claim 1 wherein the composite material is particulate filled composite material.

8. A dental restoration comprising the dental material of claim 1.

9. The dental material of claim 1 wherein the composite material follows a contour of the bar or pontic.

10. The dental material of claim 1 selected from a bridge, orthodontic appliance, space maintainer, or denture.

11. The dental material of claim 1 wherein the composite material is modified by carving, grinding, cutting or machining to a shape of a bridge, orthodontic appliance, space maintainer, or denture.

12. The dental material of claim 1 wherein the bar or pontic has a flexural strength greater than about 400 MPa.

13. The dental material of claim 1 wherein the bar or pontic has a flexural strength in the range of about 500 to about 1200 MPa.

14. A dental material comprising:
   a bar or pontic fabricated of a high strength ceramic material;
   one or more bonding layers disposed on the bar or pontic; and
   a resin material or ceramic material disposed on the one or more bonding layers;
   wherein the resin or ceramic material completely encapsulates the bar or pontic.

15. The dental material of claim 14 wherein the ceramic is comprised of at least one of alumina, zirconia, SIALON, mullite, titanium oxide, magnesium oxide, and mixtures thereof.

16. The dental material of claim 14 wherein the bonding layer has a thermal expansion that is slightly lower than a thermal expansion of the high strength ceramic material.

17. A dental restoration comprising:
   a bar or pontic fabricated of a high strength ceramic material;
   one or more ceramic bonding layers disposed on the bar or pontic; and
   a resin material or a ceramic material disposed on the one or more ceramic bonding layers;
   wherein the resin or ceramic material completely encapsulates the bar or pontic.

* * * * *